United States Patent [19]

Katner, Deceased

[11] Patent Number: 4,734,408

[45] Date of Patent: Mar. 29, 1988

[54] CRYSTALLINE CEPHALOSPORIN ANTIBIOTIC SALTS AND SOLVATES

[75] Inventor: Allen S. Katner, deceased late of Indianapolis, Ind.; by Ruth M. E. Katner, legal representative

[73] Assignee: Eli Lilly and Company, Indianapolis, Ind.

[21] Appl. No.: 943,108

[22] Filed: Dec. 17, 1986

[51] Int. Cl.[4] .................. C07D 501/36; A61K 31/545
[52] U.S. Cl. ..................................... 514/206; 540/225
[58] Field of Search ................. 540/225, 227; 514/206

[56] References Cited

U.S. PATENT DOCUMENTS

| | | | |
|---|---|---|---|
| 3,280,118 | 10/1966 | Eardsley et al. | 260/243 |
| 4,500,526 | 2/1985 | Snae et al. | 540/227 |
| 4,507,487 | 3/1985 | Kamachi et al. | 540/227 |
| 4,525,587 | 6/1985 | Chin et al. | 540/225 |

FOREIGN PATENT DOCUMENTS 0138552  4/1985  European Pat. Off. .

Primary Examiner—Nicholas S. Rizzo
Attorney, Agent, or Firm—Mary Ann Tucker; Leroy Whitaker

[57] ABSTRACT

The crystalline sulfate dihydrate, dimethylacetamide hydrate and dimethylformamide hydrate solvates of the antibiotic syn-7-[2-(2-aminothiazol-4-yl)-2-methoxyiminoacetamido]-3-(3-methyl-3H-imidazolo[4,5-c]pyridinium-5-ylmethyl)-3-cephem-4-carboxylate are provided.

6 Claims, No Drawings

CRYSTALLINE CEPHALOSPORIN ANTIBIOTIC SALTS AND SOLVATES

BACKGROUND OF THE INVENTION

This invention relates to crystalline salt and solvate forms of the antibiotic syn-7-[2-(2-aminothiazol-4-yl)-2-methoxyiminoacetamido]-3-(3-methyl-3H-imidazolo-[4,5-c]-pyridinium-5-ylmethyl)-3-cephem-4-carboxylate (the Antibiotic). The Antibiotic is described in European patent application No. 138552, published 24 April 1985, and is a broad spectrum semi-synthetic antibiotic. Salts of the Antibiotic with strong acids also are disclosed.

The Antibiotic is difficult to obtain in the highly pure form required for pharmaceutical administration and also exhibits solubility and stability characteristics which are undesirable in a drug. Therefore, a form of the Antibiotic more amenable to pharmaceutical uses is needed. In addition, it is advantageous to have intermediates which facilitate the purification of the Antibiotic.

SUMMARY

This invention provides a crystalline form of the sulfate salt of the Antibiotic. More particularly, the invention provides a crystalline dihydrate solvate of the sulfate salt which is suitable for pharmaceutical administration. The invention also provides crystalline dimethylacetamide (DMAC) hydrate and dimethylformamide (DMF) hydrate solvates of the Antibiotic, which are useful intermediates in the synthesis of the sulfate dihydrate in a highly pure state. A further embodiment is a pharmaceutical formulation comprising the sulfate dihydrate and a method of treatment employing the sulfate dihydrate.

DETAILED DESCRIPTION

The DMAC hydrate and DMF hydrate solvates of the Antibiotic tentatively have been identified as the di-DMAC dihydrate and di-DMF dihydrate forms. Analysis of the amounts of DMAC, DMF and water present in the crystals is difficult. Therefore, it is possible that one or both crystalline solvates may contain only one molecule of DMAC or DMF, or only one molecule of water.

The DMAC hydrate is a new composition of matter having the following unique X-ray powder diffraction properties when measured with a Debye-Scherrer camera using nickel-filtered copper target tube. The interplanar spacings are in the column headed "d" and the relative intensities in the column headed "I/I$_1$".

| d | I/I$_1$ |
|---|---|
| 14.03 | 0.45 |
| 9.88 | 0.85 |
| 8.71 | 0.20 |
| 7.00 | 1.00 |
| 6.39 | 0.15 |
| 6.24 | 0.20 |
| 5.56 | 0.20 |
| 5.39 | 0.80 |
| 5.05 | 0.20 |
| 4.89 | 0.25 |
| 4.65 | 0.35 |
| 4.42 | 0.35 |
| 4.20 | 0.25 |
| 4.00 | 0.35 |
| 3.90 | 0.05 |
| 3.70 | 0.20 |
| 3.56 | 0.40 |
| 3.47 | 0.40 |
| 3.34 | 0.20 |
| 3.20 | 0.10 |
| 3.09 | 0.25 |
| 2.97 | 0.10 |
| 2.75 | 0.05 |
| 2.71 | 0.05 |

The DMAC hydrate is made by suspending the Antibiotic in DMAC and adding water to give a solution. Antibiotic is added to the solution in small portions until the solution clouds. The DMAC hydrate crystallizes out of solution on standing, or crystallization can be assisted by chilling, by removing solvent, or by adding a water miscible antisolvent such as acetone, tetrahydrofuran, acetonitrile, or the like.

The DMF hydrate also is a new composition of matter having the following unique X-ray powder diffraction properties when measured with a Debye-Scherrer camera using nickel-filtered copper target tube. The interplanar spacings are in the column headed "d" and the relative intensities in the column headed "I/I$_1$". The abbreviation "b" stands for broad.

| d | I/I$_1$ |
|---|---|
| 13.92 | 0.45 |
| 9.88 | 0.91 |
| 8.76 | 0.27 |
| 7.66 | 0.18 |
| 7.03 | 1.00 |
| 6.46 | 0.09 |
| 6.15 | 0.18 |
| 5.56 | 0.45 |
| 5.32 | 0.55 |
| 5.08 | 0.55 |
| 4.86 | 0.36 |
| 4.61 | 0.36 |
| 4.42 | 0.36 |
| 4.21 | 0.18 |
| 4.00 | 0.36 |
| 3.79 | 0.09 b |
| 3.69 | 0.18 |
| 3.49 | 0.36 b |
| 3.33 | 0.09 |
| 3.16 | 0.09 |
| 3.10 | 0.27 |
| 2.92 | 0.18 |

The DMF hydrate is made by suspending the Antibiotic in DMF and adding water to give a solution. Antibiotic is added to the solution in small portions until the solution clouds. The DMF hydrate crystallizes out of solution on standing, or crystallization can be assisted by chilling, removing solvent, or adding a water miscible antisolvent such as acetone, tetrahydrofuran, acetonitrile, or the like.

Alternatively, the DMF hydrate is made by dissolving the DMAC hydrate in water and adding DMF. Similarly, the DMAC hydrate can be prepared by dissolving the DMF hydrate in water and adding DMAC.

Both the DMAC and DMF hydrates are useful intermediates in the preparation of the sulfate dihydrate. The sulfate dihydrate provided by this invention has the following unique X-ray powder diffraction properties when measured with a Debye-Scherrer camera using nickel-filtered copper target tube. The interplanar spacings are in the column headed "d" and the relative intensities in the column headed "I/I₁". The abbreviation "b" stands for broad.

| d | I/I₁ |
| --- | --- |
| 11.63 | 0.82 |
| 8.76 | 0.18 |
| 7.60 | 0.06 |
| 6.78 | 0.94 |
| 5.95 | 0.06 |
| 5.44 | 0.12 |
| 5.14 | 0.29 |
| 4.45 | 1.00 |
| 4.18 | 0.65 |
| 3.86 | 0.18 |
| 3.72 | 1.00 |
| 3.57 | 0.24 |
| 3.39 | 0.59 |
| 3.27 | 0.47 |
| 3.15 | 0.06 |
| 3.00 | 0.06 b |
| 2.74 | 0.06 b |
| 2.62 | 0.06 |
| 2.56 | 0.06 |
| 2.44 | 0.06 |
| 2.13 | 0.06 |
| 2.05 | 0.06 |

The sulfate dihydrate is made by dissolving the DMAC or DMF hydrate in aqueous sulfuric acid and chilling, removing solvent, or adding a water miscible antisolvent such as acetone, tetrahydrofuran, acetonitrile, or the like, to effect precipitation of the stable, crystalline solid. Alternatively, the sulfate dihydrate is made directly from the Antibiotic by dissolving the Antibiotic in aqueous sulfuric acid and adding an antisolvent to precipitate the crystalline solid.

Crystallization of the Antibiotic as the DMAC or DMF solvate is an effective method of removing impurities from the Antibiotic. Therefore, it is preferred to first crystallize the Antibiotic as the DMAC or DMF solvate and then recrystallize the solvate from aqueous sulfuric acid to give the crystalline sulfate dihydrate. Alternatively, the sulfate dihydrate can be first prepared and then further purified by dissolving it in water, treating the solution with a resin to remove sulfuric acid, adding DMF or DMAC to form the respective crystalline solvate, redissolving the solvate in aqueous sulfuric acid and reprecipitating the sulfate dihydrate as decribed above.

As previously described, each of the sulfate dihydrate, DMAC hydrate and DMF hydrate can be prepared directly from the Antibiotic and each is convertible to the other forms as illustrated by the following reaction scheme.

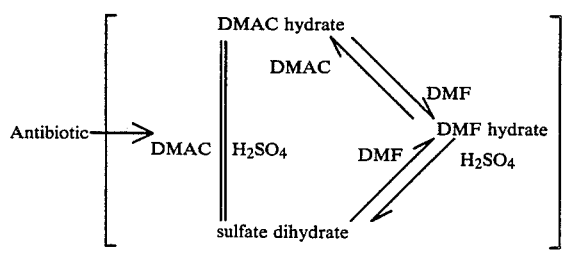

The starting material in the synthesis of the instant salt and solvates, i.e., syn-7-[2-(2-aminothiazol-4-yl)-2-methoxyiminoacetamido]-3-(3-methyl-3H-imidazolo[4,5-c]-pyridinium-5-ylmethyl)-3-cephem-4-carboxylate, the Antibiotic, is prepared by the method described in European published patent application No. 138552. In this method syn-7[2-(2-aminothiazol-4-yl)-2-methoxyiminoacetamido]-3-acetoxymethyl-3-cephem-4-carboxylic acid is reacted with N-methyl-N-trimethyl-silyltrifluoroacetamide and trimethyl-silyliodide (TMSI) to produce the corresponding 3-iodomethyl cephalosporin. The latter compound is reacted in situ with 3-methyl-3H-imidazolo[4,5-c]-pyridine to give the Antibiotic as the hydroiodide salt. The salt then is treated, for example with an ion exchange resin, to remove hydroiodic acid and yield the Antibiotic as the betaine.

PREPARATION 1 syn-7-[2-(2-Aminothiazol-4-yl)-2-methoxyiminoacetamido]-3-(3-methyl-3H-imidazolo[4,5-c]pyridinium-5-ylmethyl)-3-cephem-4-carboxylate A suspension of 91 g (200 mM) of syn-7-[2-(2-aminothiazol-4-yl)-2-methoxyiminoacetamido]-3-acetoxymethyl-3-cephem-4-carboxylic acid in 700 ml of dichloromethane containing 80 ml (450 mM) of N-methyl-N-trimethylsilyltrifluoroacetamide was warmed to 40° C. until solution occurred. The reaction mixture was cooled to 15° C. in an ice bath and stirred while 60 ml (420 mM) of TMSI were added. Stirring was continued at 25° C. for sixty minutes. The solvent was removed by evaporation under reduced pressure and the 3-iodomethylcephalosporin was dissolved in 500 ml of acetonitrile and 73 ml (900 mM) of tetrahydrofuran. To this reaction mixture was added a solution of 26.6 g (200 mM) of 3-methyl-3H-imidazolo-[4,5-c]pyridine in 100 ml of acetonitrile. The reaction mixture was stirred at 25° C. for four hours and then was added to 2000 ml of 95% acetone-methanol (v/v). The precipitated solid was collected by filtration (yield 125.7 g) and purified by reverse phase C₁₈ silica HPLC using acetonitrile-acetic acid-water (10-1-89 percent by volume). There were obtained 30.4 g of product.

IR(KBr): 1772 cm$^{-1}$;
UV (EtOH) $\lambda_{max}$ 210 mμ, $\epsilon = 36,500$;
M+Theory 529; Found 529;
NMR (DMSOd₆): signals at δ 6 9.5 (d, 1H); 9.4 (d, 1H); 9.05 (s, 1H); 8.35 (d, 1H); 7.2 (b, s, 2H); 6.73 (s, 1H); 5.75 (m, 1H); 5.15 (d, 1H); 4.15 (s, 3H); 3.83 (s, 3H).

EXAMPLE 1

Syn-7-[2-(2-aminothiazol-4-yl)-2-methoxyiminoacetamido]-3-(3-methyl-3H-imidazolo[4,5-c]-pyridinium-5-ylmethyl)-3-cephem-4-carboxylate dimethylacetamide hydrate Syn-7-[2-(2-aminothiazol-4-yl)-2-methoxyiminoacetamido]-3-(3-methyl-3H-imidazolo[4,5-c]-pyridinium-5-ylmethyl)-3-cephem-4-carboxylate, 450 mg was suspended in 6 ml of DMAC. Water was added dropwise with stirring and sonication until solution was obtained. The solution was filtered and allowed to stand at room temperature. Crystals gradually formed. After three hours the crystals were separated, washed with DMAC and dried at room temperature. There were obtained 195 mg of the crystalline DMAC hydrate having a purity of 97.3 percent as established by high performance liquid chromatography.

IR (KBr): 1775.6 cm$^{-1}$ β-lactam, 1669,5 cm$^{-1}$ amide;
UV (H₂O): $\lambda_{max}$ 210 mμ, $\epsilon = 43830.3$, $\lambda_{max}$ 260 mμ, $\epsilon = 18066.5$;

NMR (DMSOd$_6$): signals at δ 10.02 (s, 1H; 9.52 (d, 1H); 9.44 (d, 1H); 9.01 (s, 1H); 8.34 d, 1H); 7.20 (s, 2H); 6.69 (s, 1H); 5.79 (d, 1H); 5.63 (q, 1H); 5.04 (d, 1H); 5.02 (d, 1H); 4.04 (s, 3H); 3.77 (s, 3H); 3.54 (d, 1H); 3.08 (d, 1H); 2.95 (s, 3H); 2.78 (s, 3H); 1.94 (s, 3H).

EXAMPLE 2

Syn-7-[2-(2-aminothiazol-4-yl)-2-methoxyiminoacetamido]-3-(3methyl-3H-imidazolo[4,5-c]-pyridinium-5-ylmethyl)-3-cephem-4-carboxylate dimethylacetamide hydrate The procedure of Example 1 was repeated using 11 g of the Antibiotic in 90 ml DMAC and 25 ml water. Crystalline DMAC hydrate, 9.08 g, having the same properties as the product of Example 1 was obtained.

EXAMPLE 3

Syn-7-[2-(2-aminothiazol-4-yl)-2-methoxyiminoacetamido]-3-(3-methyl-3H-imidazolo4,5-c]pyridinium-5-ylmethyl)-3-cephem-4-carboxylate sulfate dihydrate DMAC hydrate, 1.0 g (1.6 mM), was dissolved in 10 ml water and 1.75 ml 1N sulfuric acid was added. Acetone was added until a precipitate formed. The solid was collected and redissolved in 2 ml water. The solvent was removed by evaporation without vacuum and fine, colorless crystals separated. The crystals were collected by filtration to give 180 mg of the crystal-line sulfate dihydrate having a purity of 99 percent as established by high performance liquid chromatography.

IR (KBr): 1792 cm$^{-1}$ β-lactam;

NMR (DMSOd$_6$): signals at δ 9.80 (s, 1H); 9.60 (d, 1H); 9.05 (s, 1H); 8.77 (d, 1H); 8.38 (d, 1H); 7.12 (s, 2H); 6.70 (s, 1H); 5.85 (q, 1H); 5.55 (q, 2H); 5.18 (d, 1H); 4.08 s(, 3H); 3.75 (s, 3H); 3.40 (q, 2H).

EXAMPLE 4

Syn-7-[2-(2-aminothiazol-4-yl)-2-methoxyiminoacetamido]-3-(3-methyl-3H-imidazolo[4,5-c]pryidinium-5-ylmethyl)-3-cephem-4-carboxylate sulfate dihydrate Antibiotic (4.0 g) was dissolved in 250 ml water and 20 ml 1N sulfuric acid was added. Solvent was removed by evaporation under reduced pressure at room temperature until about 20 ml of solution remained. Tetrahydrofuran (50 ml) was added dropwise with stirring over a period of 30 minutes. Fine white needles separated. The slurry was refrigerated overnight. The precipitate was separated by filtration, washed with tetrahydrofuran and dried at room temperature under vacuum to give 2.55 g of the sulfate dihydrate product having a purity of 97.8 percent as determined by high performance liquid chromatography and having the same properties as the product of Example 3.

EXAMPLE 5

Syn-7-[2-(2-aminothiazol-4-yl)-2-methoxyiminoacetamido]-3-(3-methyl-3H-imidazolo[4,5-c]pyridinium-5-ylmethyl)-3-cephem-4-carboxylate dimethylacetamide-hydrate Five grams of the sulfate dihydrate was dissolved in 205 ml water. IRA 68 resin, 11.5 g, was added to the solution. The slurry was stirred for about two hours and the resin removed by filtration. Solvent was removed by evaporation under reduced pressure at room temperature until an oil started to form. DMAC (35 ml) was added and the solution seeded with crystals of DMAC solvate. A thick slurry of crystals was obtained. The crystals were separated by filtration, washed with DMAC and acetone, and dried at room temperature under vacuum to give 4.35 g of the DMAC hydrate having the same properties as the product of Example 1.

EXAMPLE 6

Syn-7-[2-(2-aminothiazol-4-yl)-2-methoxyiminoacetamido]-3-(3-methyl-3H-imidazolo[4,5-c]-pyridinium-5ylmethyl)-3-cephem-4-carboxylate dimethylformamide hydrate One gram of the sulfate dihydrate was dissolved in 50 ml water. IRA 68 resin, 2.5 g, was added to the solution. The slurry was stirred for about five hours and the resin removed by filtration. Solvent was removed by evaporation under reduced pressure at room temperature until an oil was obtained. DMF (10 ml) was added and the solution seeded with crystals of DMF hydrate. Additional DMF (10 ml) was added and the solution stirred at room temperature. Crystals formed and were separated by filtration, washed with DMF, and dried at room temperature under vacuum to give 790 mg of the DMF hydrate.

NMR (DMSOd$_6$): signals at δ 10.04 (s, 1H); 9.50 (d, 1H); 9.46 (d, 1H); 9.02 (s, 1H); 8.34 (d, 1H); 7.98 (s, 1H); 7.18 (s, 2H); 6.70 (s, 1H); 5.80 (d, 1H); 5.64 (q, 1H); 5.08 (d, 1H); 5.07 (d, 1H); 4.06 (s, 3H); 3.78 (s, 3H); 3.55 (d, 1H); 3.09 (d, 1H); 2.91 (s, 3H); 2.75 (s, 3H).

EXAMPLE 7

Syn-7-[2-(2-aminothiazol-4-yl)-2-methoxyiminoacetamido]-3-(3-methyl-3H-imidazolo[4,5-c]-pyridinium-5-ylmethyl)-3-cephem-4-carboxylate dimethylformamidehydrate Four grams of DMAC hydrate were dissolved in 200 ml water. DMF, 25 ml, was added to the solution. Solvent was removed by evaporation under reduced pressure at room temperature until about 25 ml remained. DMF (25 ml) was added slowly with stirring. More solvent was removed until crystals began to form. The solution was stirred at room temperature for about three hours. Additional DMF (7 ml) was added and stirring continued for forty minutes. The crystals were separated by filtration and dried at room temperature under vacuum to give 2.82 g of DMF hydrate having the same properties as the product of Example 6.

EXAMPLE 8

Syn-7-[2-(2-aminothiazol-4-yl)-2-methoxyiminoacetamido]-3-(3-methyl-3H-imidazolo[4,5-c]pyridinium-5-ylmethyl)-3-cephem-4-carboxylate sulfate dihydrate Following the procedure of Example 3, DMF hydrate is dissolved in water containing sulfuric acid. Acetone is added until a precipitate forms. The precipitate is collected and dried to give the crystalline sulfate dihydrate.

EXAMPLE 9

Syn-7-[2-(2-aminothiazol-4-yl)-2-methoxyiminoacetamido]-3-(3-methyl-3H-imidazolo4,5-c]pyridinium-5-ylmethyl)-3-cephem-4-carboxylate dimethylacetamide hydrate Following the procedure of Example 7, DMF hydrate is dissolved in water. DMAC is added and solvent removed by evaporation until a precipitate forms. The precipitate is collected and dried to give crystalline DMAC hydrate.

EXAMPLE 10

Syn-7-[2-(2-aminothiazol-4-yl)-2-methoxyiminoacetamido]-3-(3 methyl-3H-imidazolo[4,5-c]-pyridinium-5-ylmethyl)-3-cephem-4-carboxylate dimethylformamide hydrate Following the procedure of Example 1, Antibiotic is crystallized from a water-DMF solution to give crystalline DMF hydrate.

The crystalline sulfate dihydrate provided by this invention is a therapeutically useful form of the Antibiotic. Accordingly, in a further aspect of the invention there is provided a method for treating bacterial infections in man and animals which comprises administering an antibacterially effective non-toxic amount of the crystalline Antibiotic sulfate dihydrate.

In practicing the method, the Antibiotic sulfate dihydrate may be administered in a single dose or, preferably, in multiple doses e.g., twice or three times a day. The treatment regimen may last for one day or for up to several days generally depending upon the severity of the particular infection.

Parenteral administration is preferred e.g., intravenous, intramuscular or subcutaneous, employing conventional techniques. For example, for intravenous administration the compound can be administered as a solution in a physiologically acceptable fluid such as 5% dextrose by the drip method.

An antibacterially effective amount of the Antibiotic sulfate dihydrate is an amount between about 10 mg and about 10 g. The particular dose employed in the method will depend on such factors as the nature and severity of the infection, the age and general health of the individual patient and how well the patient tolerates the Antibiotic.

The therapeutic method provided herein is useful in the treatment of infections caused by a broad spectrum of microorganisms. For example, the method is useful in treating infections caused by the gram-positive microorganisms such as staphylococcus and streptococcus and the gram-negative microorganisms such as proteus, klebsiella and pseudomonas.

The crystalline sulfate dihydrate of the invention is preferably formulated for parenteral administration, for example via the intravenous, intramuscular or subcutaneous routes. Such compositions normally will contain from about 0.05 to about 25.0 percent by weight of active ingredient. Typical excipients, diluents and carriers for parenteral formulations include isotonic saline, dilute aqueous dextrose (eg. 5%), the polyhydric aliphatic alcohols or mixtures thereof, for instance glycerin, propylene glycol, polyethylene glycol, and the like. Parenteral solutions may also contain preservatives such as phenethylalcohol, methyl and propyl parabens, thimerosal, and the like. If needed, about 0.05 to about 0.20 percent by weight of an antioxidant such as sodium metabisulfite or sodium bisulfite can also be employed. For intravenous use, preferred formulations will employ an initial concentration of about 0.5 to about 40 mg/ml of active ingredient, and for intramuscular injection, a preferred concentration of active ingredient is about 125 to about 250 mg/ml.

Examples of typical pharmaceutical formulations provided by this invention include the following.

EXAMPLE 11

| Formulation for Intravenous Use | |
| --- | --- |
| Ingredient | Amount |
| Sulfate dihydrate | 1.0 g |
| 0.9% saline | 100 ml |

The intravenous solution can be prepared, for example, with a unit dosage formulation of the crystalline sulfate dihydrate in a plastic bag or similar container, and by adding the diluent to the container prior to infusion.

EXAMPLE 12

Preparation of Parenteral Solution

In a solution of 700 ml of propylene glycol and 200 ml of distilled water for injection is dissolved 20.0 grams of the crystalline sulfate dihydrate. The pH of the solution is adjusted to 5.5 with sulfuric acid, and the volume is made up to 1000 ml with distilled water. The formulation is sterilized, filled into 5.0 ml ampoules each containing 2.0 ml (representing 40 mg of active ingredient) and sealed under nitrogen.

Pharmaceutical compositions of the invention also include unit dosage formulations. Such formulations comprise between about 200 mg and about 10 g of the crystalline sulfate dihydrate in solid form in a sterile ampoule, vial or a plastic container such as a bag adapted for i.v. administration. Such formulations may also contain a buffering agent, solubilizing agent, clarifying agent, stabilizing agent, or other excipient. An example of a pharmaceutical composition of this invention for i.v. use comprises 500 mg of the crystalline sulfate dihydrate together with an excipient, diluent or carrier in a 10 ml sterile rubber-stoppered ampoule. Another such composition comprises 4 g of crystalline sulfate dihydrate together with an excipient, diluent or carrier in a 100 ml sterile ampoule. A further composition comprises 10 g of crystalline sulfate dihydrate together with an excipient, diluent or carrier in a sealed, sterile plastic pouch.

I claim:

1. Crystalline syn-7-[2-(2-aminothiazol-4-yl)-2-methoxyiminoacetamido]-3-(3-methyl-3H-imidazolo-[4,5-c]pyridinium-5-ylmethyl)-3-cephem-4-carboxylate dimethylacetamide hydrate exhibiting essentially the following X-ray diffraction pattern:

| Spacing, d(A) | Relative Intensities, $I/I_1$ |
| --- | --- |
| 14.03 | 0.45 |
| 9.88 | 0.85 |
| 8.71 | 0.20 |
| 7.00 | 1.00 |
| 6.39 | 0.15 |
| 6.24 | 0.20 |
| 5.56 | 0.20 |
| 5.39 | 0.80 |
| 5.05 | 0.20 |
| 4.89 | 0.25 |
| 4.65 | 0.35 |
| 4.42 | 0.35 |
| 4.20 | 0.25 |
| 4.00 | 0.35 |
| 3.90 | 0.05 |
| 3.70 | 0.20 |
| 3.56 | 0.40 |
| 3.47 | 0.40 |

| Spacing, d(A) | Relative Intensities, I/I$_1$ |
|---|---|
| 3.34 | 0.20 |
| 3.20 | 0.10 |
| 3.09 | 0.25 |
| 2.97 | 0.10 |
| 2.75 | 0.05 |
| 2.71 | 0.05. |

2. Crystalline syn-7-[2-(2-aminothiazol-4-yl)-2-methoxyiminoacetamido]-3-(3-methyl-3H-imidazolo[4,5-c]-pyridinium-5-ylmethyl)-3-cephem-4-carboxylate dimethyl-formamide hydrate exhibiting essentially the following X-ray diffraction pattern:

| Spacing, d(A) | Relative Intensities, I/I$_1$ |
|---|---|
| 13.92 | 0.45 |
| 9.88 | 0.91 |
| 8.76 | 0.27 |
| 7.66 | 0.18 |
| 7.03 | 1.00 |
| 6.46 | 0.09 |
| 6.15 | 0.18 |
| 5.56 | 0.45 |
| 5.32 | 0.55 |
| 5.08 | 0.55 |
| 4.86 | 0.36 |
| 4.61 | 0.36 |
| 4.42 | 0.36 |
| 4.21 | 0.18 |
| 4.00 | 0.36 |
| 3.79 | 0.09 b |
| 3.69 | 0.18 |
| 3.49 | 0.36 b |
| 3.33 | 0.09 |
| 3.16 | 0.09 |
| 3.10 | 0.27 |

| Spacing, d(A) | Relative Intensities, I/I$_1$ |
|---|---|
| 2.92 | 0.18. |

3. Crystalline syn-7-[2-(2-aminothiazol-4-yl)-2-methoxyiminoacetamido]-3-(3-methyl-3H-imidazolo[4,5-c]-pyridinium-5-ylmethyl)-3-cephem-4-carboxylate sulfate dihydrate exhibiting essentially the following X-ray diffraction pattern:

| Spacing, d(A) | Relative Intensities, I/I$_1$ |
|---|---|
| 11.63 | 0.82 |
| 8.76 | 0.18 |
| 7.60 | 0.06 |
| 6.78 | 0.94 |
| 5.95 | 0.06 |
| 5.44 | 0.12 |
| 5.14 | 0.29 |
| 4.45 | 1.00 |
| 4.18 | 0.65 |
| 3.86 | 0.18 |
| 3.72 | 1.00 |
| 3.57 | 0.24 |
| 3.39 | 0.59 |
| 3.27 | 0.47 |
| 3.15 | 0.06 |
| 3.00 | 0.06 b |
| 2.74 | 0.06 b |
| 2.62 | 0.06 |
| 2.56 | 0.06 |
| 2.44 | 0.06 |
| 2.13 | 0.06 |
| 2.05 | 0.06. |

4. A pharmaceutical formulation comprising the compound of claim 3 and a pharmaceutical excipient, diluent or carrier.

5. The formulation of claim 4 in a form suitable for parenteral administration.

6. A method of treating bacterial infections comprising administering to a subject an antibacterial amount of the compound of claim 3.

* * * * *